(12) United States Patent
Phelps et al.

(10) Patent No.: US 8,759,053 B2
(45) Date of Patent: Jun. 24, 2014

(54) MICROBIALLY-MEDIATED METHOD FOR SYNTHESIS OF NON-OXIDE SEMICONDUCTOR NANOPARTICLES

(75) Inventors: Tommy J. Phelps, Knoxville, TN (US); Robert J. Lauf, Oak Ridge, TN (US); Ji Won Moon, Oak Ridge, TN (US); Adam J. Rondinone, Arlington, VA (US); Lonnie J. Love, Knoxville, TN (US); Chad Edward Duty, Knoxville, TN (US); Andrew Stephen Madden, Norman, OK (US); Yiliang Li, Discovery Bay (HK); Ilia N. Ivanov, Knoxville, TN (US); Claudia Jeanette Rawn, Knoxville, TN (US)

(73) Assignees: UT-Battelle, LLC, Oak Ridge, TN (US); University of Tennessee Research Foundation, Knoxville, TN (US)

( * ) Notice: Subject to any disclaimer, the term of this patent is extended or adjusted under 35 U.S.C. 154(b) by 332 days.

(21) Appl. No.: 12/364,638

(22) Filed: Feb. 3, 2009

(65) Prior Publication Data
US 2010/0193752 A1 Aug. 5, 2010

(51) Int. Cl.
*C12P 3/00* (2006.01)
*C01B 17/00* (2006.01)
*C01B 19/00* (2006.01)
*C01G 9/00* (2006.01)
*C01B 11/00* (2006.01)
*H01B 1/00* (2006.01)

(52) U.S. Cl.
USPC ............ 435/168; 252/518.1; 252/519.4; 423/99; 423/508; 423/509; 423/512.1; 423/514; 977/895

(58) Field of Classification Search
USPC ............ 252/500–521.6; 423/445 R, 99, 508, 423/509, 512.1, 514; 435/168; 977/895
See application file for complete search history.

(56) References Cited

U.S. PATENT DOCUMENTS

| 4,954,231 A | 9/1990 | Correia et al. |
| 6,444,453 B1 | 9/2002 | Lauf et al. |

(Continued)

FOREIGN PATENT DOCUMENTS

CN 1710082 A * 6/2005 ............... C12P 3/00

OTHER PUBLICATIONS

Bai et al. ("Biological synthesis of semiconductor zinc sulfide nanoparticles by immobilized *Rhodobacter sphaeroides*." Biotechnol Lett, vol. 28, p. 1135-1139, pub online Jun. 23, 2006).*

(Continued)

*Primary Examiner* — Tri V Nguyen
(74) *Attorney, Agent, or Firm* — Scully, Scott, Murphy & Presser, P.C.

(57) ABSTRACT

The invention is directed to a method for producing non-oxide semiconductor nanoparticles, the method comprising: (a) subjecting a combination of reaction components to conditions conducive to microbially-mediated formation of non-oxide semiconductor nanoparticles, wherein said combination of reaction components comprises i) anaerobic microbes, ii) a culture medium suitable for sustaining said anaerobic microbes, iii) a metal component comprising at least one type of metal ion, iv) a non-metal component containing at least one non-metal selected from the group consisting of S, Se, Te, and As, and v) one or more electron donors that provide donatable electrons to said anaerobic microbes during consumption of the electron donor by said anaerobic microbes; and (b) isolating said non-oxide semiconductor nanoparticles, which contain at least one of said metal ions and at least one of said non-metals. The invention is also directed to non-oxide semiconductor nanoparticle compositions produced as above and having distinctive properties.

19 Claims, 7 Drawing Sheets

(56) References Cited

U.S. PATENT DOCUMENTS

| | | | |
|---|---|---|---|
| 7,060,473 | B2 | 6/2006 | Phelps et al. |
| 2002/0187889 | A1 | 12/2002 | Lauf et al. |
| 2006/0014261 | A1 | 1/2006 | Phelps et al. |
| 2008/0108749 | A1 | 5/2008 | Chen |
| 2009/0155876 | A1 | 6/2009 | Hur et al. |
| 2010/0160521 | A1* | 6/2010 | Curran et al. ............... 524/402 |
| 2010/0184179 | A1 | 7/2010 | Rondinone et al. |
| 2010/0193752 | A1 | 8/2010 | Phelps et al. |
| 2010/0330367 | A1* | 12/2010 | Phelps et al. ............... 428/402 |

OTHER PUBLICATIONS

Zhang et al. ("Formation of single-domain magnetite by a thermophilic bacterium." American Mineralogist, vol. 83, pp. 1409-1418, 1998).*

Mandal et al. ("The use of microorganisms for the formation of metal nanoparticles and their application." Appl Microbiol Biotechnol, vol. 69, p. 485-492, pub online Nov. 2005).*

Bai et al. ("Microbial synthesis of semiconductor lead sulfide nanoparticles using immobilized *Rhodobacter sphaeroides*." Materials Letters, vol. 63, p. 764-766, pub online Jan. 7, 2009).*

Cunningham et al. ("Precipitation of Cadmium by *Clostridium thermoaceticum*." Appl and Envir Microb, p. 7-14, Jan. 1993).*

Pearce C.I. et al., "Microbial Manufacture of Chalcogenide-Based Nanoparticles Via the Reduction of Selenite Using *Veillonella atypica:* an In Situ EXAFS Study", *Nanotechnology 19*:1-13 (2008).

Eisenstein M., "Bacteria Find Work as Amateur Chemists", *Nature Methods 2*(1):6-7 (Jan. 2005).

Bowman J.P. et al., "*Shewanella gelidimarina* Sp. Nov. and *Shewanella frigidimarina* Sp. Nov., Novel Antarctic Species With the Ability to Produce Eicosapentaenoic Acid (20:5ω3) and Grow Anaerobically by Dissimilatory Fe(III) Reduction", *International Journal of Systematic Bacteriology 47*(4):1040-1047 (1997).

Darugar Q. et al., "Observation of Optical Gain in Solutions of CdS Quantum Dots at Room Temperature in the Blue Region", *Applied Physics Letters 88*:261108-1-261108-3 (2006).

Li Y-L et al., "Reduction of Iron Oxides Enhanced by a Sulfate-Reducing Bacterium and Biogenic $H_2S$", *Geomicrobiology Journal 23*:103-117 (2006).

Lovley D.R. et al., "*Geobacter metallireducens* Gen. Nov. Sp. Nov., a Microorganism Capable of Coupling the Complete Oxidation of Organic Compounds to the Reduction of Iron and Other Metals", *Arch. Microbiol 159*:336-344 (1993).

Smith P.R. et al., "Photophysical and Photochemical Characterisation of Bacterial Semiconductor Cadmium Sulfide Particles", *J. Chem. Soc., Faraday Trans. 94*(9):1235-1241 (1998).

Kieft T.L. et al., "Dissimilatory Reduction of Fe(III) and Other Electron Acceptors by a *Thermus* Isolate", *Applied and Environmental Microbiology 65*(3):1214-1221 (1999).

Dameron C.T. et al., "Biosynthesis of Cadmium Sulphide Quantum Semiconductor Crystallites", *Nature 338*:596-597 (1989).

International Search Report and Written Opinion dated Mar. 2, 2012 received from the Korean Intellectual Property Office from related International Application No. PCT/US2011/049317.

Yu W.W. et al., "Experimental Determination of the Extinction Coefficient of CdTe, CdSe, and CdS Nanocrystals", Chem. Mater. 15(14):2854-2860 (Jun. 2003).

Final Official Action dated Oct. 8, 2013 in a related application, namely, U.S. Appl. No. 12/874,522.

U.S. Official Action dated Feb. 26, 2014 in a related application, namely, U.S. Appl. No. 12/357,523.

\* cited by examiner

MICROBIALLY-MEDIATED METHOD FOR SYNTHESIS OF NON-OXIDE SEMICONDUCTOR NANOPARTICLES

This invention was made with government support under Contract Number DE-AC05-00OR22725 between the United States Department of Energy and UT-Battelle, LLC. The United States government has certain rights in this invention.

FIELD OF THE INVENTION

The present invention relates to the field of microbial synthesis of inorganic materials, and more particularly, microbial synthesis of non-oxide semiconductor nanoparticles.

BACKGROUND OF THE INVENTION

Nanoparticles having metal non-oxide compositions (i.e., "semiconductor" or "quantum dot" nanoparticles) are increasingly being used in numerous emerging applications. Some of these applications include electronics (e.g., transistors and diode lasers), LED displays, photovoltaics (e.g., solar cells), and medical imaging. Quantum dot nanoparticles are also being investigated as powerful new computer processing elements (i.e., qubits). Semiconductor nanoparticles often possess a metal chalcogenide composition, such as CdSe and ZnS.

As a consequence of its small size, the electron band structure of a quantum dot differs significantly from that of the bulk material. In particular, significantly more of the atoms in the quantum dot are on or near the surface, in contrast to the bulk material in which most of the atoms are far enough removed from the surface so that a normal band structure predominates. Thus, the electronic and optical properties of a quantum dot are related to its size. In particular, photoluminescence is size dependent.

Several physical methods are known for synthesizing semiconductor nanoparticles. Some of the physical techniques include advanced epitaxial, ion implantation, and lithographic techniques. The physical techniques are generally useful for producing minute amounts of semiconductor nanoparticles with well-defined (i.e., tailor-made, and typically, uniform) morphological, electronic, magnetic, or photonic characteristics. The physical techniques are typically not useful for synthesizing semiconductor nanoparticles in commercially significant quantities (e.g., grams or kilograms).

Several chemical processes are also known for the production of semiconductor nanoparticles. Some of these methods include arrested precipitation in solution, synthesis in structured media, high temperature pyrolysis, and sonochemical methods. For example, cadmium selenide can be synthesized by arrested precipitation in solution by reacting dialkylcadmium (i.e., $R_2Cd$) and trioctylphosphine selenide (TOPSe) precursors in a solvent at elevated temperatures, i.e.,

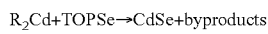

$R_2Cd+TOPSe \rightarrow CdSe+byproducts$

High temperature pyrolysis of semiconductor nanoparticles generally entails preparing an aerosol containing a mixture of volatile cadmium and selenium precursors, and then subjecting the aerosol to high temperatures (e.g., by carrying through a furnace) in the presence of an inert gas. Under these conditions, the precursors react to form the semiconductor nanoparticles (e.g., CdSe) and byproducts.

Though the chemical processes described above are generally capable of producing semiconductor nanoparticles in more significant quantities, the processes are generally energy intensive (e.g., by generally requiring heating and a post-annealing step), and hence, costly. Accordingly, commercially significant amounts of the resulting nanoparticles tend to be prohibitively expensive. Furthermore, these processes tend to be significantly limited with respect to control of the physical (e.g., size, shape, and crystalline form) and electronic or photonic characteristics of the resulting nanoparticles.

The microbial synthesis of semiconductor nanoparticles is known. See, for example, P. R. Smith, et al., *J. Chem. Soc., Faraday Trans.*, 94(9), 1235-1241 (1998) and C. T. Dameron, et al., *Nature*, 338: 596-7, (1989). However, there are significant obstacles that prevent such microbially-mediated methods from being commercially viable. For example, current microbial methods are generally limited to the production of semiconductor nanoparticles on a research scale, i.e., an amount sufficient for elucidation by analytical methods. In addition, current microbial processes generally produce semiconductor nanoparticles adhered to cell membranes. Accordingly, numerous separation and washing steps are generally needed.

Accordingly, there is a need in the art for a microbial method for the synthesis of semiconductor nanoparticles capable of producing semiconductor nanoparticles on a commercial (i.e., bulk) scale at a non-prohibitive cost. There is also a need for a microbial method of synthesis which provides substantially pure semiconductor nanoparticle product bereft of microbial matter, thereby reducing or eliminating separation and washing steps. There is also a particular need for such a microbial method of synthesis whereby characteristics of the nanoparticles (e.g., particle size, morphology, electronic or photonic characteristics, dopant composition, and doping level) are more precisely or uniformly controlled.

SUMMARY OF THE INVENTION

In one aspect, the invention is directed to a microbially-mediated method for the production of semiconductor nanoparticles. The method described herein can advantageously produce a variety of semiconductor nanoparticle compositions on a commercially viable scale. In addition, the method can advantageously produce semiconductor nanoparticles of a particular particle size, morphology, electronic or photonic characteristic, dopant composition, or doping level.

In a preferred embodiment, the method involves: (a) subjecting a combination of reaction components to conditions conducive to microbially-mediated formation of non-oxide semiconductor nanoparticles, wherein the combination of reaction components includes i) anaerobic microbes (i.e., "microbes"), ii) a culture medium suitable for sustaining the anaerobic microbes, iii) a chalcophile metal component (i.e., "metals" or "metal component") containing at least one type of metal ion, iv) a non-metal component containing at least one non-metal selected from the group consisting of S, Se, Te, and As, and v) one or more electron donors that provide donatable electrons to the anaerobic microbes during consumption of the electron donor by the anaerobic microbes; and (b) isolating said non-oxide semiconductor nanoparticles, which contain at least one of the metal ions and at least one of the non-metals.

In another aspect, the invention is directed to a nanoparticulate semiconductor composition produced by the above method. In a preferred embodiment the nanoparticles produced by the above method are single-crystalline and have an average size ranging from about 1, 2 or 3 nm to about 20 nm.

The semiconductor composition also preferably possesses a photoluminescence peak characterized by a full-width half maximum value of or less than about 20 nm.

The invention advantageously provides a method capable of producing pure semiconductor nanoparticles on a commercial (i.e., bulk) scale at a non-prohibitive cost. A further particular advantage of the method is that it provides the capability of synthesizing semiconductor nanoparticles having selected photoluminescent characteristics over a wide range of such characteristics. For example, by controlling the size, shape, composition, and/or crystalline structure of the nanoparticles, the location or width of the photoluminescence peak can be accordingly controlled or fine-tuned over a wide range.

Numerous electronic and photonic devices can benefit from such precise control of the photoluminescent properties of semiconductor nanoparticles. In particular, photovoltaic devices are currently limited by the use of photoluminescent materials that are not tunable, or semi-tunable with great difficulty. Yet, there is a clear and present need in the art of photovoltaic devices for photoluminescent-tunable materials. Other types of devices that can benefit from such tunable materials include light-emitting and laser diodes. Accordingly, the method and compositions of the invention can greatly advance several types of devices, including photovoltaic devices.

DETAILED DESCRIPTION OF THE INVENTION

Figure 1:
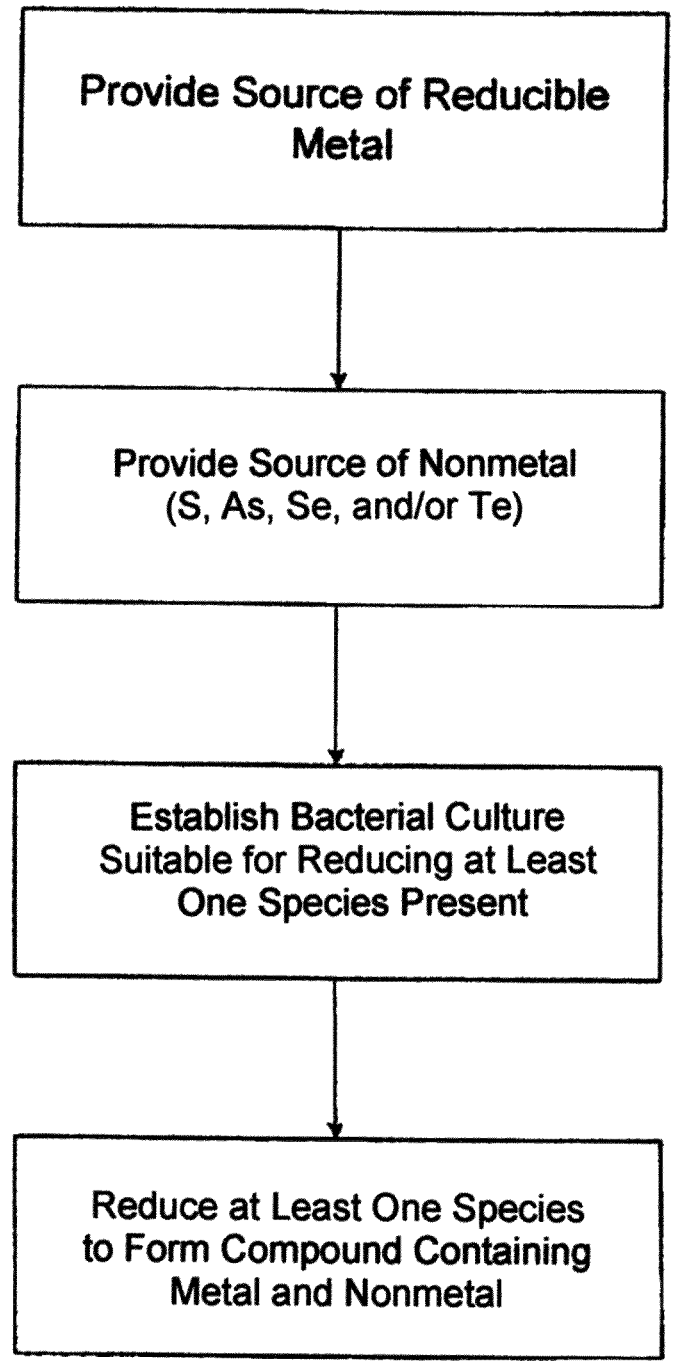
FIG. 1. A process diagram illustrating a preferred embodiment of the invention for forming metal chalcogenide crystalline nanoparticles.

The non-oxide semiconductor nanoparticles (i.e., "semiconductor" or "quantum dot" nanoparticles) produced herein are those containing one or more chalcophile metals in a positive oxidation state, and one or more non-metals selected from sulfur (S), selenium (Se), tellurium (Te), and arsenic (As), in a negative oxidation state. Some examples of suitable metals include, for example, V, Cr, Mn, Fe, Co, Ni, Cu, Zn, Mo, W, Pd, Pt, Au, Ag, Cd, Hg, Ga, In, Tl, Ge, Sn, Pb, Sb, and Bi. Some particularly preferred metals include Cd, Cu, Fe, Ga, In, and Zn. Some examples of semiconductor nanoparticle compositions include CdS, CdSe, CdTe, $Cd_3As_2$, ZnS, ZnSe, ZnTe, $Zn_3As_2$, $Ga_2S_3$, $Ga_2Se_3$, $Ga_2Te_3$, GaAs, $In_2S_3$, $In_2Se_3$, $In_2Te_3$, InAs, CuS, CuSe, CuTe, $Cu_3As_2$, FeSe, $Fe_3As_2$, FeAs, PbS, PbSe, PbTe, $Pb_3As_2$, HgS, HgSe, HgTe, $Cd_xZn_{1-x}Te$, $Cd_xHg_{1-x}Te$, $Hg_xZn_{1-x}Te$, $Cd_xZn_{1-x}Se$, $Cd_xHg_{1-x}Se$, $Hg_xZn_{1-x}Se$, $Pb_xSn_{1-x}Te$, $Ga_xIn_{2-x}Se_3$, $Ga_xIn_{1-x}As$, $CuIn_xGa_{1-x}S_2$ (e.g., $CuIn_{0.5}Ga_{0.5}S$ or $CuIn_{0.4}Ga_{0.6}S_2$), $CuGaS_2$, $CuInS_2$, $CuIn_xGa_{1-x}Se_2$ (e.g., $CuIn_{0.5}Ga_{0.5}Se_2$ or $CuIn_{0.4}Ga_{0.6}Se_2$), $CuGaSe_2$, and $CuInSe_2$, wherein x is an integral or non-integral numerical value greater than 0 and less than or equal to 1. One or more dopant metals can also be included in the composition.

The semiconductor nanoparticles have a size (i.e., "diameter" for spherical or polyhedral nanoparticles) in the nanoscale regime, i.e., less than 1 micron (1μm). In different embodiments, the nanoparticles can have at least one dimension of at least 1 nm, 2 nm, 3 nm, 4 nm, 5 nm, 10 nm, 12 nm, 15 nm, 20 nm, 25 nm, 30 nm, 40 nm, 50 nm, 100 nm, 200 nm, 300 nm, 400 nm, or 500 nm, or any range therebetween (e.g., 1-10, 2-10, 1-20, 2-20, or 3-20 nm), or between any of the foregoing values and up to or less than 1 μm. In one embodiment, the nanoparticles are fairly disperse in size (e.g., having a size variation of 20% or greater from a median size). In another embodiment, the nanoparticles are fairly monodisperse in size (e.g., having a size variation less than 20% from a median size).

The semiconductor nanoparticles can also have any suitable morphology. Some examples of possible nanoparticle shapes include amorphous, fibrous, tubular, cylindrical, rod, needle, spherical, ovoidal, pyramidal, cuboidal, rectangular, dodecahedral, octahedral, plate, and tetrahedral. Often, the semiconductor nanoparticles are equiaxed euhedral crystals (i.e., typically cubes, octahedra, and modifications thereof).

In a preferred embodiment, the semiconductor nanoparticles possess a photoluminescence peak characterized by a full-width half maximum (FWHM) value of about or less than 20 nanometers (20 nm). In different embodiments, the semiconductor nanoparticles possess a photoluminescence peak having a FWHM value of about or less than 15 nm, 10 nm, 8 nm, or 5 nm. In different embodiments, the photoluminescence peak is preferably located at 300 nm, 320 nm, 340 nm, 360 nm, 380 nm, 400 nm, 420 nm, 440 nm, 460 nm, 480 nm, 500 nm, 520 nm, 540 nm, or 560 nm, or within 10 or 20 nm of any of these values (e.g., 435-445 nm or 430-450 nm), or within a range bounded by any of these values (e.g., 400-500 nm).

In a particular aspect, the invention is directed to a method for producing the semiconductor nanoparticles described above. In the method, a precursor chalcophile metal component (i.e., one that can form semiconducting chalcogenide compounds) and a precursor non-metal component (i.e., "non-metal component") are processed by anaerobic microbes in a manner that produces non-oxide semiconductor nanoparticles.

The precursor metal component contains one or more types of metals in ionic form, particularly as described above. The one or more metals is typically in the form of a salt or coordination compound, or a colloidal hydrous metal oxide or mixed metal oxide, wherein "compound" as used herein also includes a "material" or "polymer". Some examples of precursor metal compounds applicable herein include the metal halides (e.g., $CdCl_2$, $ZnCl_2$, $ZnBr_2$, $GaCl_3$, $InCl_3$), metal nitrates (e.g., $Cd(NO_3)_2$, $Ga(NO_3)_3$, and $Fe(NO_3)_3$), metal perchlorates, metal carbonates (e.g., $CdCO_3$), metal sulfates (e.g., $CdSO_4$, $FeSO_4$, and $ZnSO_4$), metal oxides (e.g., $Fe_2O_3$, CdO, $In_2O_3$, ZnO), metal hydroxides (e.g., $Fe(OH)_3$ and $Zn(OH)_2$), metal oxyhydroxides (e.g., FeOOH, or FeO(OH), and their alternate forms), metal-EDTA complexes, metal amines (e.g., metal alkylamine, piperidine, pyridine, or bipyridine salt complexes), metal carboxylates (e.g., cadmium acetate), and metal acetylacetonate (i.e., metal-acac) complexes. One or more dopant species can be included in the precursor metal component in order to likewise dope the resulting nanoparticles.

When more than one metals are used as precursors, the molar ratio of metal ions can be adjusted such that a particular molar ratio of metals is provided in the nanoparticle product. Typically, the molar ratio of metal ions in the metal component is the molar ratio of metals found in the nanoparticle product. However, the molar ratio of metals in the product may, in several embodiments, differ from the molar ratio of metals in the metal component. In a particular embodiment, a desired molar ratio of metals is achieved in the nanoparticle product by suitable adjustment of metal ratios in the precursor metal component.

The total metal concentration should be below a concentration at which the metals are toxic to the microbes being used. Typically, the total metal concentration is no more than 100 mM. In different embodiments, the total metal concentration may preferably be no more than 90 mM, 80 mM, 70 mM, 60 mM, 50 mM, 40 mM, 30 mM, 20 mM, 15 mM, 10 mM, 5 mM, 1 mM, 0.5 mM, or 0.1 mM, or within a range resulting from any two of the above exemplary values.

The precursor non-metal component provides the resulting nanoparticle composition with one or more non-metals selected from S, Se, Te, and As. The non-metal component can include any suitable form of these non-metals, including, for example, the elemental or compound forms of these non-metals.

In a first embodiment, the non-metal component includes a sulfur-containing compound. In one instance, the sulfur-containing compound is an inorganic sulfur-containing compound. Some examples of inorganic sulfur-containing compounds include the inorganic sulfates (e.g., $Na_2SO_4$, $K_2SO_4$, $MgSO_4$, $(NH_4)_2SO_4$, $H_2SO_4$, or a metal sulfate), the inorganic sulfites (e.g., $Na_2SO_3$, $H_2SO_3$, or $(NH_4)SO_3$), inorganic thiosulifates (e.g., $Na_2S_2O_3$ or $(NH_4)_2S_2O_3$), sulfur dioxide, peroxomonosulfate (e.g., $Na_2SO_5$ or $KHSO_5$), and peroxodisulfate (e.g., $Na_2S_2O_8$, $K_2S_2O_8$, or $(NH_4)_2S_2O_8$). In another instance, the sulfur-containing compound is an organosulfur (i.e., organothiol or organomercaptan) compound. The organosulfur compound contains at least one hydrocarbon group and is typically characterized by the presence of at least one sulfur-carbon bond. Some examples of suitable organosulfur compounds include the hydrocarbon mercaptans (e.g., methanethiol, ethanethiol, propanethiol, butanethiol, thiophenol, ethanedithiol, 1,3-propanedithiol, 1,4-butanedithiol, thiophene), the alcohol-containing mercaptans (e.g., 2-mercaptoethanol, 3-mercaptopropanol, 4-mercaptophenol, and dithiothreitol), the mercapto-amino acids (e.g., cysteine, homocysteine, methionine, thioserine, thiothreonine, and thiotyrosine), mercapto-peptides (e.g., glutathione), the mercapto-pyrimidines (e.g., 2-thiouracil, 6-methyl-2-thiouracil, 4-thiouracil, 2,4-dithiouracil, 2-thiocytosine, 5-methyl-2-thiocytosine, 5-fluoro-2-thiocytosine, 2-thiothymine, 4-thiothymine, 2,4-dithiothymine, and their nucleoside and nucleotide analogs), the mercapto-purines (e.g., 6-thioguanine, 8-thioadenine, 2-thioxanthine, 6-thioxanthine, 6-thiohypoxanthine, 6-thiopurine, and their nucleoside and nucleotide analogs), the thioethers (e.g., dimethylsulfide, diethylsulfide, diphenylsulfide, biotin), the disulfides (e.g., cystine, lipoic acid, diphenyl disulfide, iron disulfide, and 2-hydroxyethyldisulfide), the thiocarboxylic acids (e.g., thioacetic acid), the thioesters, the sulfonium salts (e.g., trimethylsulfonium or diphenylmethylsulfonium chloride), the sulfoxides (e.g., dimethylsulfoxide), the sulfones (e.g., dimethylsulfone), thioketones, thioamides, thiocyanates, isothiocyanates, thiocarbamates, dithiocarbamates, and trialkylphosphine sulfide (e.g., trioctylphosphine sulfide), thiourea compounds, or any of the inorganic sulfur-containing compounds, such as those enumerated above, which have been modified by inclusion of a hydrocarbon group.

In a second embodiment, the non-metal component includes a selenium-containing compound. In one instance, the selenium-containing compound is an inorganic selenium-containing compound. Some examples of inorganic selenium-containing compounds include the inorganic selenates (e.g., $Na_2SeO_4$, $K_2SeO_4$, $MgSeO_4$, $(NH_4)_2SeO_4$, $H_2SeO_4$, or a metal selenate), the inorganic selenites (e.g., $Na_2SeO_3$, $H_2SeO_3$, or $(NH_4)_2SeO_3$), inorganic selenosulfates (e.g., $Na_2SSeO_3$ or $(NH_4)_2SSeO_3$), selenium dioxide, and selenium disulfide. In another instance, the selenium-containing compound is an organoselenium compound. The organoselenium compound contains at least one hydrocarbon group and is typically characterized by the presence of at least one selenium-carbon bond. Some examples of suitable organoselenium compounds include the hydrocarbon selenols (e.g., methaneselenol, ethaneselenol, n-propaneselenol, isopropaneselenol, and selenophenol (benzeneselenol)), the selenoamino acids (e.g., selenocysteine, selenocystine, selenohomocysteine, selenomethionine), the seleno-pyrimidines (e.g., 2-selenouracil, 6-methyl-2-selenouracil, 4-selenouracil, 2,4-diselenouracil, 2-selenocytosine, 5-methyl-2-selenocytosine, 5-fluoro-2-selenocytosine, 2-selenothymine, 4-selenothymine, 2,4-diselenothymine, and their nucleoside and nucleotide analogs), the seleno-purines (e.g., 6-selenoguanine, 8-selenoadenine, 2-selenoxanthine, 6-selenoxanthine, 6-selenohypoxanthine, 6-selenopurine, and their nucleoside and nucleotide analogs), the selenides (e.g., dimethylselenide, diethylselenide, and methylphenyselenide), the diselenides (e.g., dimethyldiselenide, diethyldiselenide, and diphenyldiselenide), the selenocarboxylic acids (e.g., selenoacetic acid, selenopropionic acid), the selenosulfides (e.g., dimethylselenosulfide), the selenoxides (e.g., dimethylselenoxide and diphenylselenoxide), the selenones, the selenonium salts (e.g., dimethylethylselenonium chloride), the vinylic selenides, selenopyrylium salts, trialkylphosphine selenide (e.g., trioctylphosphine selenide, i.e., TOPSe), selenourea compounds, or any of the inorganic selenium-containing compounds, such as those enumerated above, which have been modified by inclusion of a hydrocarbon group.

In a third embodiment, the non-metal component includes a tellurium-containing compound. In one instance, the tellurium-containing compound is an inorganic tellurium-containing compound. Some examples of inorganic tellurium-containing compounds include the inorganic tellurates (e.g., $Na_2TeO_4$, $K_2TeO_4$, $MgTeO_4$, $(NH_4)_2TeO_4$, $H_2TeO_4$, $H_6TeO_6$, or a metal tellurate), the inorganic tellurites (e.g., $Na_2TeO_3$), and tellurium dioxide. In another instance, the tellurium-containing compound is an organotellurium compound. The organotellurium compound contains at least one hydrocarbon group and is typically characterized by the presence of at least one tellurium-carbon bond. Some examples of suitable organotellurium compounds include the hydrocarbon tellurols (e.g., methanetellurol, ethanetellurol, n-propanetellurol, isopropanetellurol, and tellurophenol (benzenetellurol)), the telluro-amino acids (e.g., tellurocysteine, tellurocystine, tellurohomocysteine, telluromethionine), the telluropyrimidines and their nucleoside and nucleotide analogs (e.g., 2-tellurouracil), the telluro-purines and their nucleoside and nucleotide analogs, the tellurides (e.g., dimethyltelluride, diethyltelluride, and methylphenyltelluride), the ditellurides (e.g., dimethylditelluride, diethylditelluride, and diphenylditelluride), the telluroxides (e.g., dimethyltelluroxide and diphenyltelluroxide), the tellurones, the telluronium salts, the vinylic tellurides, telluropyrylium salts, tellurourea compounds, 24-telluracholestanol, or any of the inorganic tellurium-containing compounds, such as those enumerated above, which have been modified by inclusion of a hydrocarbon group.

In a fourth embodiment, the non-metal component includes an arsenic-containing compound. In one instance, the arsenic-containing compound is an inorganic arsenic-containing compound. Some examples of inorganic arsenic-containing compounds include the inorganic arsenates (e.g., $Na_3AsO_4$, $Na2HAsO4$, $NaH_2AsO_4$, $H_3AsO_4$, $Mg_3(AsO_4)_2$, 1-arseno-3-phosphoglycerate, or a transition metal arsenate), inorganic arsenites (e.g., $Na_3AsO_3$, $Na2HAsO3$, $NaH_2AsO_3$, $H_3AsO_3$, $Ag_3AsO_3$, $Mg_3(AsO_3)_2$), and arsenic oxides (e.g., $As_2O_3$ and $As_2O_5$), and arsenous carbonate (i.e., $As_2(CO_3)_3$). In another instance, the arsenic-containing compound is an organoarsine compound. The organoarsine compound is characterized by the presence of at least one hydrocarbon group and at least one arsenic atom. Some examples of suitable organoarsine compounds include the hydrocarbon arsines (e.g., trimethylarsine, triethylarsine, triphenylarsine, arsole, and 1,2-bis(dimethylarsino)benzene), arsenic-derivatized sugars (e.g., glucose 6-arsenate), arsonic acids (e.g., phenylarsonic acid, 4-aminophenylarsonic acid, 4-hydroxy-3-nitrobenzenearsonic acid, 2,3,4-trihydroxybutylarsonic acid, arsonoacetic acid, diphetarsone, diphenylarsinic acid, and 3-arsonopyruvate), arseno-amino acids and their derivatives (e.g., 3-arsonoalanine, arsenophenylglycine, and arsenate tyrosine), organoarsine oxides (e.g., metlylarsine oxide, 4-aminophenylarsenoxide, oxophenylarsine, and oxophenarsine), 10,10'-oxybis-10H-phenoxarsine, 1-arseno-3-phosphoglycerate, arsenobetaine, arsenocholine, arsenotriglutathione, or any of the inorganic arsenic-containing compounds, such as those enumerated above, which have been modified by inclusion of a hydrocarbon group.

Preferably, the non-metal compound is not a reduced sulfide (e.g., $Na_2S$, $K_2S$, $H_2S$, or $(NH_4)_2S$), reduced selenide (e.g., $H_2Se$ or $(NH_4)_2Se$), reduced telluride (e.g., $H_2Te$ or $(NH_4)_2Te$), or reduced arsenide compound. As known in the art, such reduced compounds have a propensity for precipitating various metals from solution. Since direct reaction of the non-metal compound and metal to form a precipitate is preferably avoided in the method, a reduced non-metal compound is preferably used under conditions where an adverse reaction or precipitation does not occur.

The anaerobic microbes considered herein are any microbes known in the art capable of forming semiconductor nanoparticles from one or more types of metal ions and one or more non-metals selected from S, Se, Te, and As. The microbe can be, for example, a eukaryotic or procaryotic (and either unicellular or multicellular) type of microbe having this ability. Of particular relevance herein are the procaryotic organisms, which are predominantly unicellular, and are divided into two domains: the bacteria and the archaea. The microbes can be, in addition, fermentative, metal-reducing, dissimilatory, sulfate-reducing, thermophilic, mesophilic, psychrophilic, or psychrotolerant. The microbes are preferably those capable of directly reducing (i.e., without the use of chemical means) a sulfur-containing, selenium-containing, tellurium-containing, or arsenic-containing compound to, respectively, a sulfide (i.e., $S^{2-}$)-containing, selenide (i.e., $Se^{2-}$)-containing, telluride (i.e., $Te^{2-}$)-containing, or arsenide (i.e., $As^{3-}$)-containing compound, such as $H_2S$ or a salt thereof Preferably, the microbes are capable of reducing the sulfur-, selenium-, tellurium-, or arsenic-containing compound without intermediate production of, respectively, elemental sulfur, selenium, tellurium, or arsenic.

In one embodiment, the microbes considered herein are thermophilic, i.e., those organisms capable of thriving at temperatures of at least about 40° C. (and more typically, at least 45° C. or 50° C.) and up to about 100° C. or higher temperatures. Preferably, the thermophilic microbes are either bacteria or archaea, and particularly, those possessing an active hydrogenase system linked to high energy electron carriers.

A group of thermophilic bacteria particularly considered herein are the species within the genus *Thermoanaerobacter*. A particular species of *Thermoanaerobacter* considered herein is *Thermoanaerobacter* strain TOR-39, a sample of which was deposited with the American Type Culture Collection (10801 University Blvd., Manassas, Va. 20010) on Sep. 7, 2001 as accession number PTA-3695. Strain TOR-39 is a thermophile that grows optimally at temperatures from about 65 to 80° C. The conditions needed to grow and maintain this strain, including basal medium, nutrients, vitamins, and trace elements are detailed in U.S. Pat. No. 6,444,453, the entire contents of which are incorporated herein by reference. Some particular strains of *Thermoanaerobacter ethanolicus* particularly considered herein include *T. ethanolicus* strain C1 and *T. ethanolicus* strain M3.

Another group of thermophilic bacteria particularly considered herein are the species within the class Thermococci. An order of Thermococci particularly considered herein is Thermococcales. A family of Thermococcales particularly considered herein is Thermococcaceae. A genus of Thermococcaceae particularly considered herein is *Thermococcus*. A species of *Thermococcus* particularly considered herein is *Thermococcus litoralis*.

Another group of thermophilic bacteria particularly considered herein are the species within the genus *Thermoterrabacterium*. A species of *Thermoterrabacterium* particularly considered herein is *Thermoterrabacterium ferrireducens*, and particularly, strain JW/AS-Y7.

Still another group of thermophilic bacteria particularly considered herein are the species within the phylum *Deinococcus-Thermus*. A class of *Deinococcus-Thermus* particularly considered herein is *Deinococci*. An order of *Deinococci* particularly considered herein is Thermales. A genus of Thermales particularly considered herein is *Thermus*. A species of *Thermus* particularly considered herein is *Thermus* sp. strain SA-01.

Other thermophilic bacteria particularly considered herein include thermophilic species within any of the genera *Thermoanaerobacterium* (e.g., *T. thermosulfurigenes, T. polysaccharolyticum, T. zeae, T. aciditolerans,* and *T. aorearoense*), *Bacillus* (e.g., *B. infernus*), *Clostridium* (e.g., *C. thermocellum*), *Anaerocellum* (e.g., *A. thermophilum*), *Dictyoglomus* (e.g., *D. thermophilum*), and *Caldicellulosiruptor* (e.g., *C. acetigenus, C. hydrothermalis, C. kristjanssonii, C. kronotskiensis, C. lactoaceticus, C. owensensis,* and *C. saccharolyticus*).

In another embodiment, the microbes considered herein are mesophilic (e.g., organisms thriving at moderate temperatures of about 15-40° C.) or psychrophilic (e.g., organisms thriving at less than 15° C.). As used herein, the term psychrophilic also includes "psychrotolerant". Psychrophilic bacteria are typically found in deep marine sediments, sea ice, Antarctic lakes, and tundra permafrost. Some examples of such microbes include species within the genera *Shewanella* (e.g., *S. alga* strain PV-1, *S. alga*, PV-4, *S. pealeana*, W3-7-1, *S. geldimarina,* and *S. frigidimarina*), *Clostridium* (e.g., *C. frigoris, C. lacusfryxellense, C. bowmanii, C. psychrophilum, C. laramiense, C. estertheticum,* and *C. schirmacherense*),

*Bacillus* (e.g., *B. psychrosaccharolyticus, B. insolitus, B. globisporus, B. psychrophilus, B. cereus, B. subtilis, B. circulans, B. pumilus, B. macerans, B. sphaericus, B. badius, B. licheniformis, B. firmus, B. globisporus,* and *B. marinus*), and *Geobacter* (e.g., *G. sulfurreducens, G. bemidjiensis,* and *G. psychrophilus*). Of particular interest are those strains capable of anaerobic growth with nitrate as an electron acceptor.

In yet another embodiment, the microbes considered herein are sulfur-reducing (e.g., sulfate- or sulfite-reducing) microbes. In a preferred embodiment, the sulfur-reducing microbes are one or more species selected from *Desulfovibrio* (e.g., *D. desulfuricans, D. gigas, D. salixigens,* and *D. vulgaris*), *Desulfolobus* (e.g., *D. sapovorans* and *D. propionicus*), *Desulfotomaculum* (e.g., *D. thermocisternum, D. thermobenzoicum, D. auripigmentum, D. nigrificans, D. orientis, D. acetoxidans, D. reducens,* and *D. ruminis*), *Desulfomicrobium* (e.g., *D. aestuarii, D. hypogeium,* and *D. salsuginis*), *Desulfomusa* (e.g., *D. hansenii*), *Thermodesulforhabdus* (e.g., *T. norvegica*) the order Desulfobacterales, and more particularly, the family Desulfobacteraceae, and more particularly, the genera *Desulfobacter* (e.g., *D. hydrogenophilus, D. postgatei, D. giganteus, D. halotolerans,* and *D. vibrioformis*), *Desulfobacterium* (e.g., *D. indolicum, D. anilini, D. autotrophicum, D. catecholicum, D. cetonicum, D. macestii, D. niacini, D. phenolicum, D. vacuolatum*), *Desulfobacula* (e.g., *D. toluolica* and *D. phenolica*), *Desulfobotulus* (*D. sapovorans* and *D. marinus*), *Desulfocella* (e.g., *D. halophila*), *Desulfococcus* (e.g., *D. multivorans* and *D. biacutus*), *Desulfofaba* (e.g., *D. gelida* and *D. fastidiosa*), *Desulfofrigus* (e.g., *D. oceanense* and *D. fragile*), *Desulfonema* (e.g., *D. limicola, D. ishimotonli,* and *D. magnum*), *Desulfosarcina* (e.g., *D. variabilis, D. cetonica,* and *D. ovata*), *Desulfospira* (e.g., *D. joergensenii*), *Desulfotalea* (e.g., *D. psychrophila* and *D. arctica*), and *Desulfotignum* (*D. balticum, D. phosphitoxidans,* and *D. toluenicum*). Several of the sulfur-reducing microbes are either thermophilic or mesophilic. The sulfur-reducing microbes may also be psychrophilic or psychrotolerant.

In still other embodiments, the microbes considered herein are selenium-reducing (e.g., selenate- or selenite-reducing), tellurium-reducing (e.g., tellurate- or tellurite-reducing), or arsenic-reducing (e.g., arsenate- or arsenite-reducing). In one embodiment, the selenium-, tellurium-, or arsenic-reducing microbe is one of the sulfur-reducing microbes described above. In another embodiment, the selenium- or tellurium-reducing microbe is selected from other microbes not described above, e.g., *Thauera selenatis, Sulfospirillum barnesii, Selenihalanerobacter shriftii, Bacillus selenitireducens, Pseudomonas stutzeri, Enterobacter hormaechei, Klebsiella pneumoniae,* and *Rhodobacter sphaeroides*. In yet another embodiment, the arsenic-reducing microbe is selected from any of the microbes described above, or in particular, from *Sulfurospirillum arsenophiturn* or *Geospirillum arsenophilus*. It will also be appreciated that, in addition to the exemplary microorganisms listed above, other types of cultures, including mixed microbial cultures or uncharacterized microbial cultures from natural enviromnents, and the like, may also be used in the invention. For example, cultures not yet characterized from natural hot springs where various metals are known to be present can demonstrate suitably high metal-reducing or selenium-reducing activity to carry out the inventive methods even though the exact species or genus of the microbes may be unknown and more than one species or genus may be present in said culture.

The microbes can also be dissimilatory iron-reducing bacteria. Such bacteria are widely distributed and include some species in at least the following genera: *Bacillus, Deferribacter, Desulfuromonas, Desulfuromusa, Ferrimonas, Geobacter, Geospirillum, Geovibrio, Pelobacter, Sulfolobus, Thermoanaerobacter, Thermoanaerobium, Thermoterrabacterium,* and *Thermus*.

The choice of microbe generally involves trade-offs relating to cost, efficiency, and properties of the nanoparticle product. For example, thermophiles may be preferred when more product per unit of time is the primary consideration, since a high temperature process generally produces product at a faster rate. Conversely, psychrophilic or psychrotolerant microbes may be preferred in a case where one or more improved characteristics are of primary consideration, and where the improved characteristics are afforded to the product by virtue of the cooler process.

The microbes used in the method described herein can be obtained and cultured by any of the methods known in the art. Some of the general processes by which such bacteria may be used is taught in U.S. Pat. Nos. 6,444,453 and 7,060,473, the entire disclosures of which are incorporated herein by reference. The isolation, culturing, and characterization of thermophilic bacteria are described in, for example, T. L. Kieft et al., "Dissimilatory Reduction of Fe(III) and Other Electron Acceptors by a *Thermus* Isolate," *Appl. and Env. Microbiology,* 65 (3), pp. 1214-21 (1999). The isolation, culture, and characterization of several psychrophilic bacteria are described in, for example, J. P. Bowman et al., "*Shewanella gelidimarina* sp. nov. and *Shewanella frigidimarina* sp. nov., Novel Antarctic Species with the Ability to Produce Eicosapentaenoic Acid (20:5ω3) and Grow Anaerobically by Dissimilatory Fe(III) Reduction," *Int. J. of Systematic Bacteriology* 47 (4), pp. 1040-47 (1997). The isolation, culture, and characterization of mesophilic bacteria are described in, for example, D. R. Lovley et al., "*Geobacter metallireducens* gen. nov. sp. nov., a microorganism capable of coupling the complete oxidation of organic compounds to the reduction of iron and other metals," *Arch. Microbiol.,* 159, pp. 336-44 (1993), the disclosure of which is incorporated herein by reference in its entirety.

The culture medium for sustaining the microbes can be any of the known aqueous-based media known in the art useful for this purpose. The culture medium may also facilitate growth of the microbes. As is well known in the art, the culture medium includes such components as nutrients, trace elements, vitamins, and other organic and inorganic compounds, useful for the sustainment or growth of microbes.

In the method of the invention, the microbes are provided with at least one electron donor. An electron donor is any compound or material capable of being oxidatively consumed by the microbes such that donatable electrons are provided to the microbes by the consumption process. The produced electrons are used by the microbes to reduce one or more non-metal compounds and/or metal ions.

In one embodiment, the electron donor includes one or more carboxylate-containing compounds that can be oxidatively consumed by the microbes. Some examples of suitable carboxylate-containing compounds include formate, acetate, propionate, butyrate, oxalate, malonate, succinate, fumarate, glutarate, lactate, pyruvate, glyoxylate, glycolate, and citrate.

In another embodiment, the electron donor includes one or more sugars (i.e., saccharides, disaccharides, oligosaccharides, or polysaccharides) that can be oxidatively consumed by the microbes. Some examples of suitable sugars include glucose, fructose, sucrose, galactose, maltose, mannose, arabinose, xylose, lactose, and disaccharides therefrom, oligosaccharides therefrom, or polysaccharides therefrom.

In another embodiment, the electron donor includes one or more inorganic species that can be oxidatively consumed by the microbes. The inorganic species can be, for example, an oxidizable gas, such as hydrogen or methane. Such gases can be oxidized by hydrogen-consuming or methane-consuming microbes which have the capacity to reduce one or more metals or non-metal compounds by the produced electrons.

The five reaction components described above (i.e., anaerobic microbes, culture medium, metal component, non-metal component, and electron donor component) are combined in a suitable container and subjected to conditions (e.g., temperature and reaction time) suitable for producing the nanoparticles from the reaction components. A preferred process is shown in a flow diagram of FIG. 1. In one embodiment, the container for holding the reaction components is simple by containing no more than container walls, a bottom, and a lid. In another embodiment, the container is more complex by including additional features, such as inlet and outlet elements for gases, liquids, or solids, one or more heating elements, nanoparticle separation features (e.g., traps or magnets), one or more agitating elements, fluid recirculating elements, electronic controls for controlling one or more of these or other conditions, and so on.

The components may be combined in any suitable manner. For example, each of the five reaction components or a combination thereof (e.g., the anaerobic microbes and cell culture) may be prepared before the components are combined, or alternatively, obtained in a pre-packaged form before the components are combined. When components or combinations thereof are provided in package form, the packaged forms may be designed to be used in their entireties, or alternatively, designed such that a portion of each is used (e.g., as aliquots of a concentrate).

In one embodiment, the reaction components are combined immediately before the reaction components are subjected to suitable reaction conditions for producing semiconductor nanoparticles. This embodiment is particularly useful for the case when the reaction components react on contact with each other (i.e., upon being combined) to produce nanoparticles.

In another embodiment, at least two of the reaction components are substantially unreactive with each other such that they can be in a combined state for a substantial period of time before use without significant degradation or production of nanoparticles. The substantial period of time is preferably a conventional time of storage (e.g., at least one week, one month, three months, six months, or a year). This embodiment can be beneficial by simplifying the process, specifically, by lessening the number of addition steps (i.e., less than five). In a particular embodiment, a solution containing at least three or four of the components is storage-stable under specified conditions (e.g., reduced temperature). Production of nanoparticles can begin when the remaining one or two components are added, and after the combination is subjected to conditions conducive to microbially-mediated formation of semiconductor nanoparticles. Alternatively, a solution containing all of the components is storage-stable. When production of nanoparticles is desired, the solution is subjected to conditions conducive to microbially-mediated formation of semiconductor nanoparticles. In addition, storage-stable samples of the reaction components can be provided in the form of a kit. The samples in the kit can contain individual or combined reaction components.

The method is practiced by subjecting the combined components to conditions that induce the formation of semiconductor nanoparticles therefrom. Some of the conditions that can affect formation of semiconductor nanoparticles from the combined components include temperature, reaction time, precursor metal concentration, pH, and type of microbes used. In some embodiments, the reaction conditions may not require any special measures other than combining the reaction components at room temperature (e.g., 15-25° C.) and waiting for nanoparticles to grow over a period of time. In other embodiments, the combined reaction components are, for example, either heated, cooled, or modified in pH, in order to induce nanoparticle formation.

When thermophilic microbes are used, the temperature at which the reaction is conducted can preferably be at least, for example, 40° C., 45° C., 50° C., 55° C., 60° C., 65° C., 70° C., 75° C., 80° C., 85° C., or 90° C. depending on the type of thermophilic microbes being used. Any range resulting from any two of the foregoing values is also contemplated herein. When mesophilic microbes are used, the temperature can preferably be at least 15° C., 20° C., 25° C., or 30° C., and up to any of the temperatures given above for thermophilic microbes. When psychrophilic microbes are used, the temperature at which the reaction is conducted can preferably be less than, for example, 40° C., or at or less than 35° C., 30° C., 25° C., 20° C., 15° C., 10° C., 50° C., 0° C., or –5° C., or any range resulting from any two of the foregoing values. It is to be appreciated that, even though different exemplary temperatures have been given for each type of microbe, each type of microbe may be capable of thriving in temperatures well outside the typical temperatures given above. For example, a thermophilic microbe may also be capable of thriving to a useful extent at temperatures below 40° C. where mesophilic microbes traditionally thrive; or mesophilic or thermophilic microbes may be capable of thriving to a useful extent at temperatures below 15° C. (i.e., by being psychrotolerant in addition to mesophilic or thermophilic). Particularly when employing *Thermoanaerobacter* sp. strain TOR-39, the temperature is preferably maintained between about 45° C. and 75° C.

The reaction (incubation) time is the period of time that the combined reaction components are subjected to reaction conditions necessary for producing nanoparticles. The reaction time is very much dependent on the other conditions used, as well as the characteristics desired in the nanoparticle product. For example, shorter reaction times (e.g., 1-60 minutes) may be used at elevated temperature conditions whereas longer reaction times (e.g., 1-7 days, or 1-3 weeks) may be used at lower temperatures to obtain a similar yield of product. Typically, shorter reaction times produce smaller particles than particles produced using longer reaction times under the same conditions. The incubation may be, for example, between 3 and 30 days, depending on the amount and size of the crystalline nanoparticle product desired.

The pH can also be suitably adjusted. Generally, when using thermophilic bacteria, the pH value is preferably within the range of 6.5-9. For example, particularly when employing *Thermoanaerobacter* sp. strain TOR-39, the pH is preferably maintained at a level between about 6.9 and 7.5. In different embodiments, depending on the microbe and other conditions, the pH is preferably acidic by being less than 7 (e.g., a pH of or less than 6.5, 6.0, 5.5, 5.0, 4.5, 4.0, 3.5, 3.0, 2.5, 2.0, 1.5, 1.0, or a range resulting from any two of these values), or preferably alkaline by being above 7 (e.g., a pH of or greater than 7.5, 8.0, 8.5, 9.0, 9.5, 10, 10.5, 11, 11.5, or a range resulting from any two of these values), or preferably approximately neutral by having a pH of about 7, e.g., 6.5-7.5.

In addition to selecting reaction conditions (e.g., temperature, reaction time, and pH) on the basis of permitting or inducing the formation of nanoparticles, the reaction conditions can also be selected for numerous other purposes, including to modify or optimize the product yield, production efficiency, particle size or size range, particle composition or phase (e.g., crystalline vs. semicrystalline vs. amorphous), or particle morphology. For example, lower reaction temperatures may be employed to provide a more pure or single-crystalline product.

Once the nanoparticles are produced, they are isolated (i.e., separated) from the reaction components and byproducts formed by the reaction products. Any method known in the art for separation of nanoparticles from reaction components can be used herein.

In one embodiment, nanoparticles are separated from the reaction components by allowing the nanoparticles to settle to the bottom of the container and then decanting the liquid medium or filtering off the nanoparticle product. The collected crystalline nanoparticle product may be washed one or more times to further purify the product. The reaction container may optionally be fitted with a drain valve to allow the solid product to be removed without decanting the medium or breaking gas seals.

In another embodiment, the container in which the reaction components are housed is attached to (or includes) an external trap from which the crystalline nanoparticle product can be removed. The trap is preferably in the form of a recess situated below flowing reaction solution. Nanoparticles in the flowing reaction solution are denser than the reaction solution, and hence, will settle down into the trap. The flowing reaction solution is preferably recirculated.

In another embodiment, a filter is used to trap the nanoparticles. The filter can be in the form of multiple filters that trap successively smaller particles. Depending on the particle size and other variables, one or more filters that trap the nanoparticles may contain a pore size of no more than about 0.5, 0.4, 0.3, 0.25, 0.2, 0. 1, or 0.05 µm.

In yet another embodiment, in the case where the nanoparticle product is magnetic, a magnetic source (e.g., electromagnet or other suitable magnetic field-producing device) can be employed to collect the nanoparticles. The magnetic source can be used as the sole means of separation, or used in combination with other separation means, such as a trap or filter.

The method of the invention can be performed in a batchwise manner or in a continuous manner. Examples of suitable arrangements for performing the method of the invention in a continuous manner are described in U.S. Pat. No. 6,444,453, particularly FIGS. 3 and 4 therein, all of which is incorporated by reference herein. Because the nanoparticles tend to grow larger the longer they remain in the culture, continuous collection of nanoparticle product from a recirculating fluid may be used as a means of controlling particle size. In addition, the degree of fluid circulation (e.g., flow rate) can be modulated to promote shedding of the nanoparticles from the microbes.

The method may include one or more chemicals that can facilitate reduction of one or more non-metal compounds or metal ions. However, the production of nanoparticles remains microbially-mediated. Therefore, conditions are avoided in which non-metal compounds and/or metal ions are chemically (i.e., directly) reduced such that semiconductor nanoparticles are produced without microbial mediation. Some of the conditions that can affect whether nanoparticle production is direct or microbially-mediated includes the absence or presence of a chemical reductant, the choice of chemical reductant, the processing temperature, and the choice of microbes. The method described herein preferably excludes the use of strong reductants because such reductants may have the ability to directly reduce one or more metal ions or non-metal compounds before microbial consumption can take place. As used herein, a "strong reductant" is meant to be a chemical stronger in reducing power than the known weaker reductants, such as citrate, reducing sugars, alcohols, and hydrogen gas, under standard conditions. Some examples of chemical reductants preferably excluded from use in the method include the hydrides (e.g., borohydrides and aluminum hydrides), hydrazines, hypophosphorous acid, and Sn(II) metal salts. It is understood that weaker reductants, such as the exemplary ones given, may also be unsuitable for the method described herein if conditions are provided that render these reductants capable of directly reducing non-metal compounds or metal ions (e.g., by use of temperatures high enough to cause direct reduction as the main reductive process).

Preferably, the method of the invention excludes the use of a mediator, such as anthraquinone disulfonic acid (AQDS). Furthermore, in one embodiment, one or more stabilizing (i.e., surface-active) compounds or materials (e.g., glutathione, 2-mercaptoethanol, triphenylphosphine, or other surface-active mercaptan or phosphine compound) is used in the method for stabilizing or controlling the size of the produced nanoparticles. In another embodiment, stabilizing compounds are excluded in the method, whereby the produced chalcogenide nanoparticles are sufficiently stable in the absence of a stabilizing compound or material.

Examples have been set forth below for the purpose of illustration and to describe certain specific embodiments of the invention. However, the scope of this invention is not to be in any way limited by the examples set forth herein.

EXAMPLE 1

Preparation of ZnS Nanoparticles Using Sulfate-Reducing Microbes

A mesophilic sulfate-reducing strain *Desulfovibrio* G-20 was grown in a lactate/$SO_4$ culture medium as taught generally by Li et al., "Reduction of iron oxides enhanced by a sulfate-reducing bacterium and biogenic $H_2S$", *Geomicrobiol. J.*, 23:103-117 (2006), the entire disclosure of which is incorporated herein by reference. $Zn^{2+}$ was added as $ZnCl_2$ at 0.2 mM and well-formed highly crystalline ZnS (sphalerite phase) nanoparticles were formed. Precipitated semi-conductor materials were harvested by repeated centrifugation followed by one or more times of washing with deionized water. Particle size was estimated at approximately 5.9 nm. A similar experimental run using standard medium containing nutrients, vitamins, trace elements, lactate as an electron donor at 50 mM, and $Na_2SO_4$ as a non-metal component with 50 mM and with $Zn^{2+}$ added as $ZnCl_2$ at 5 mM yielded ZnS particles estimated at approximately 3.7 nm in size.

The forgoing example demonstrates that the sulfate-reducing strain G-20 was able to make the target ZnS phase in a desirable size range. The product nanoparticles were formed externally to the cells, making it easy to separate the product without killing the bacteria. Significantly, these nanoparticles were fluorescent, as expected for quantum dots of this size and composition.

EXAMPLE 2

Preparation of CdS Nanoparticles Using Sulfate-Reducing Microbes

CdS nanoparticles were synthesized using the same mesophilic sulfate-reducing strain *Desulfovibrio* G-20. In this case, $CdCl_2$ as a precursor metal component was added at 0.06 mM and a sulfur-containing non-metal compound as 0.06 mM Na$_2$SO$_3$ based on CO$_3$-buffered medium containing nutrients, vitamins, trace elements, and lactate as an electron donor at 50 mM. Precipitated nanoparticles were harvested by repeated centrifugation followed by one or more times washing with deionized water. Well-formed highly crystalline CdS nanoparticles with an extremely sharp fluorescence peak as shown in FIG. 5C were formed.

The forgoing example demonstrates that the sulfate-reducing strain G-20 was able to make the target CdS phase in the desired size range. Remarkably, the process showed no deleterious toxicity of Cd on the bacteria used. Again, the product nanoparticles were formed externally to the cells, making it easy to separate the product without killing the bacteria. These nanoparticles had exceptionally good photoluminescence, e.g., exceptionally sharp photoluminescent peaks. The exceptionally sharp photoluminescent peak exhibited by the inventive quantum dot materials may arise through one or more factors that have not as yet been conclusively identified. Without intending to restrict the invention in any way or to limit the invention to any particular theoretical mechanism, it is conjectured that a very sharp (or narrow) photoluminescent peak could be attributed to any of the following: (1) more uniform particle size distribution; (2) more uniform particle-to-particle chemical composition; (3) more chemical homogeneity within each particle; (4) fewer point defects (particularly vacancies); and (5) more uniform particle morphology. Regardless of the exact mechanism(s), it is observed that batches of particles made by the inventive technique exhibit batch properties that are clearly superior to previously reported quantum dot products.

EXAMPLE 3

Preparation of ZnS Nanoparticles Using Metal-Reducing Microbes

In an effort to demonstrate the generality of the process, the following series of experiments were performed using a metal-reducing strain of bacteria rather than a sulfate-reducing strain. Fluorescent ZnS nanoparticles were synthesized using the thermophilic metal-reducing strain TOR-39 cultured in low-NaCl medium for one month. Because TOR-39 cannot efficiently reduce sulfate per se, sulfur-containing non-metal component was added in the form of thiosulfate. Zn was added as ZnCl$_2$. One experiment used 5 mM thiosulfate and 5 mM ZnCl$_2$, added as sequential aliquots (1 mM/day). A second experiment used 10 mM thiosulfate and 10 mM ZnCl$_2$, added as sequential aliquots (1 mM/day). The two experiments produced highly crystalline ZnS quantum dots with average particle sizes of 6.5 nm and 12 nm, respectively.

This surprising result may be interpreted as follows. Although TOR-39 is a metal-reducing bacterium (e.g., typically reducing Fe$^{3+}$ to Fe$^{2+}$), in this case the metal was Zn$^{2+}$, which is not microbially reducible. However, the TOR-39 apparently reduced thiosulfate, thereby providing sufficient sulfide to form the desired ZnS phase. As in the previous examples, the sulfide nanoparticles were produced externally to the cell; they had broad photoluminescent peaks centered at 460 to 480 nm. TOR-39 has other desirable characteristics, notably the fact that it is thermophilic and grows optimally at around 65° C., making the culture fairly insensitive to contamination by bacteria from the environment, most of which would die at this process temperature.

EXAMPLE 4

Preparation of CdS Nanoparticles Using Metal-Reducing Microbes

CdS nanoparticles were synthesized using the same thermophilic metal-reducing strain TOR-39 as in the previous example, using a modified TOR-39 medium (without bicarbonate buffer and mineral solution). Applicants have found that using NaHCO$_3$ buffer caused the precipitation of Cd carbonate (otavite), so buffering with NaOH and MOPS is preferred. Recognizing that TOR-39 cannot reduce sulfate, several sulfur-containing non-metal sources were used as shown in the following table.

Table showing CdS production by TOR-39 Using Different Sulfur Substrates

| S source | Concentration | Cd concentration | Precipitates[a] |
|---|---|---|---|
| cysteine-S | 0.5 mL/day | 5 ppm/day | Haw |
| cysteine-S | 0.5 mL/day | 5 ppm/day | Haw |
| thiosulfate | 10 mM | 5 ppm/day | Haw + Gre |
| sulfite | 10 mM | 5 ppm/day | Haw + Gre |
| thiosulfate | 10 mM | 30 ppm/day | Haw + Gre |
| thiosulfate | 10 mM | 100 ppm/day | Haw + Gre |

[a]Haw = hawleyite and Gre = greenockite

The series of experiments in the above example demonstrates, surprisingly, that fermentative strain TOR-39 can produce CdS quantum dots using a number of organic sulfur sources, and furthermore, did not suffer any adverse effects from Cd concentrations up to 100 ppm per day. The quantum dots produced in these runs showed superior photoluminescence. For example, samples made using cysteine-S at 0.5 mL/day and Cd at 5 ppm/day showed a sharp photoluminescent peak at ~440 nm and broader photoluminescence at ~550 nm. Another sample prepared using thiosulfate at 10 mM and Cd at 5 ppm/day showed a photoluminescent peak at ~440 nm with a FWHM of about 10 nm as shown in FIG. 5A. This value represents a nearly three-fold improvement over reported properties for conventionally-prepared materials.

EXAMPLE 5

Preparation of Nanoparticles of Composition CuIn$_{0.5}$Ga$_{0.5}$S$_2$

A series of experiments were run to synthesize particles having the nominal composition CuIn$_{0.5}$Ga$_{0.5}$S$_2$. Cultures of *Thermoanaerobacter* sp. strain TOR-39 were cultured in "FeS medium", which is based on the standard TOR-39 culture medium as taught, e.g., in U.S. Pat. No. 6,444,453 but without NaHCO$_3$ buffer, but with approximately 15 mM MOPS (i.e., 3-(N-morpholino)propanesulfonic acid sodium salt or 4-morpholinepropanesulfonic acid sodium salt). MOPS at a 1.5 M stock solution was titrated to pH ~8.0 with 10 N NaOH and added to the culture medium at a final concentration of ~15 mM to prevent carbonate formation, at 65° C. for three weeks. The electron donor was 10 mM glucose. Thiosulfate concentration was 10 mM. Metal stock solution consisted of cupric or cuprous chloride, indium chloride, and gallium chloride in molar ratios of 2:1:1, so that a 0.2 M stock solution has 0.2, 0.1, and 0.1 M Cu, In, and Ga, respectively. Metals were typically added at the rate of 0.2 mM (copper basis) per day in order to avoid toxicity to the bacteria.

Figure 7:
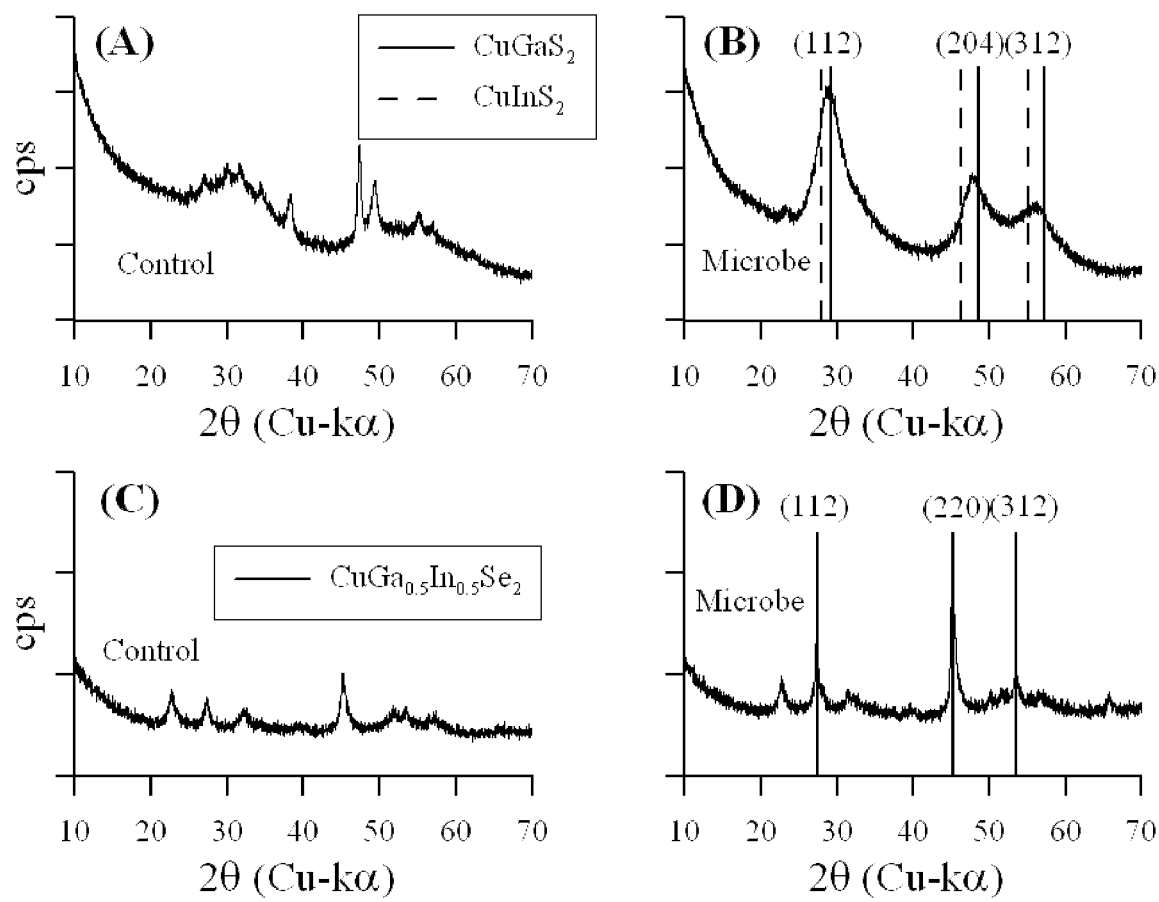
FIGS. 7A-7D. X-ray diffraction results for: $CuGaS_2$ or $CuInS_2$ product made without microbes (FIG. 7A); $CuGaS_2$ or $CuInS_2$ product made with TOR-39 microbes (FIG. 7B); $CuIn_{0.5}Ga_{0.5}Se_2$ product made without microbes (FIG. 7C); and $CuIn_{0.5}Ga_{0.5}Se_2$ product made with microbes.

X-ray diffraction results confirmed that control samples (i.e., without microbes) did not produce the desired phase as shown in FIG. 7A. Well-defined diffraction lines were seen in the batches containing TOR-39, corresponding to the (112), (204) and (312) reflections of $CuGaS_2$ or $CuInS_2$ as shown in FIG. 7B. The crystallite size was estimated to be about 3 nm. It was further found that using a cupric source produced a higher yield than using a cuprous source (i.e., CuCl) and that yields as high as 300 mg per liter of medium could be obtained.

Based on the foregoing results, the skilled artisan will appreciate that substitutions of other metals (or modifications of the In:Ga ratio) may be carried out though routine experimentation. Similarly, substitutions of organoselenium compounds may be used to synthesize analogous selenide particles.

EXAMPLE 6

Preparation of Nanoparticles of Composition $CuIn_{0.5}Ga_{0.5}Se_2$

A series of experiments were run to synthesize particles having the nominal composition $CuIn_{0.5}Ga_{0.5}Se_2$. Cultures of *Thermoanaerobacter* sp. strain M1 were cultured in "FeS medium", which is based on the standard TOR-39 culture medium as taught, e.g., in U.S. Pat. No. 6,444,453 but with 15 mM MOPS buffer as described above. The electron donor was 10 mM glucose. Sodium selenite concentration was 5 mM. Metal stock solution consisted of cupric chloride, indium chloride, and gallium chloride in molar ratios of 2:1:1, so that a 0.2 M stock solution has 0.2, 0.1, and 0.1 M Cu, In, and Ga, respectively. Metals were typically added at the rate of 0.25 mM (copper basis) per day in order to avoid toxicity to the bacteria.

Precipitated nanoparticles were harvested by repeated centrifugation followed by one or more times washing with deionized water without lysing, then freeze dried for further phase identification using XRD. X-ray diffraction results confirmed that control samples (i.e., without microbes) did not produce the desired phase in FIG. 7C. Well-defined diffraction lines were seen in the microbial batches, corresponding to the (112), (220) and (312) reflections of $CuIn_{0.5}Ga_{0.5}Se_2$ as shown in FIG. 7D. In another experiment utilizing an uncharacterized thermophilic anaerobic culture growing at 65 C, ten discrete fractional additions of metals were added over a period of fourteen days. After a total of three weeks of incubation the culture produced $CuIn_{0.3}Ga_{0.7}Se_2$ which exhibited clear XRD peaks.

Based on the foregoing results, the skilled artisan will appreciate that substitutions of other metals (or modifications of the In:Ga ratio) and the reduction of secondary phases may be carried out through routine experimentation. Similarly, substitutions of organoselenium compounds may be used to synthesize analogous selenide particles.

EXAMPLE 7

A Batch-Type Bioprocessing Reactor

Figure 2:
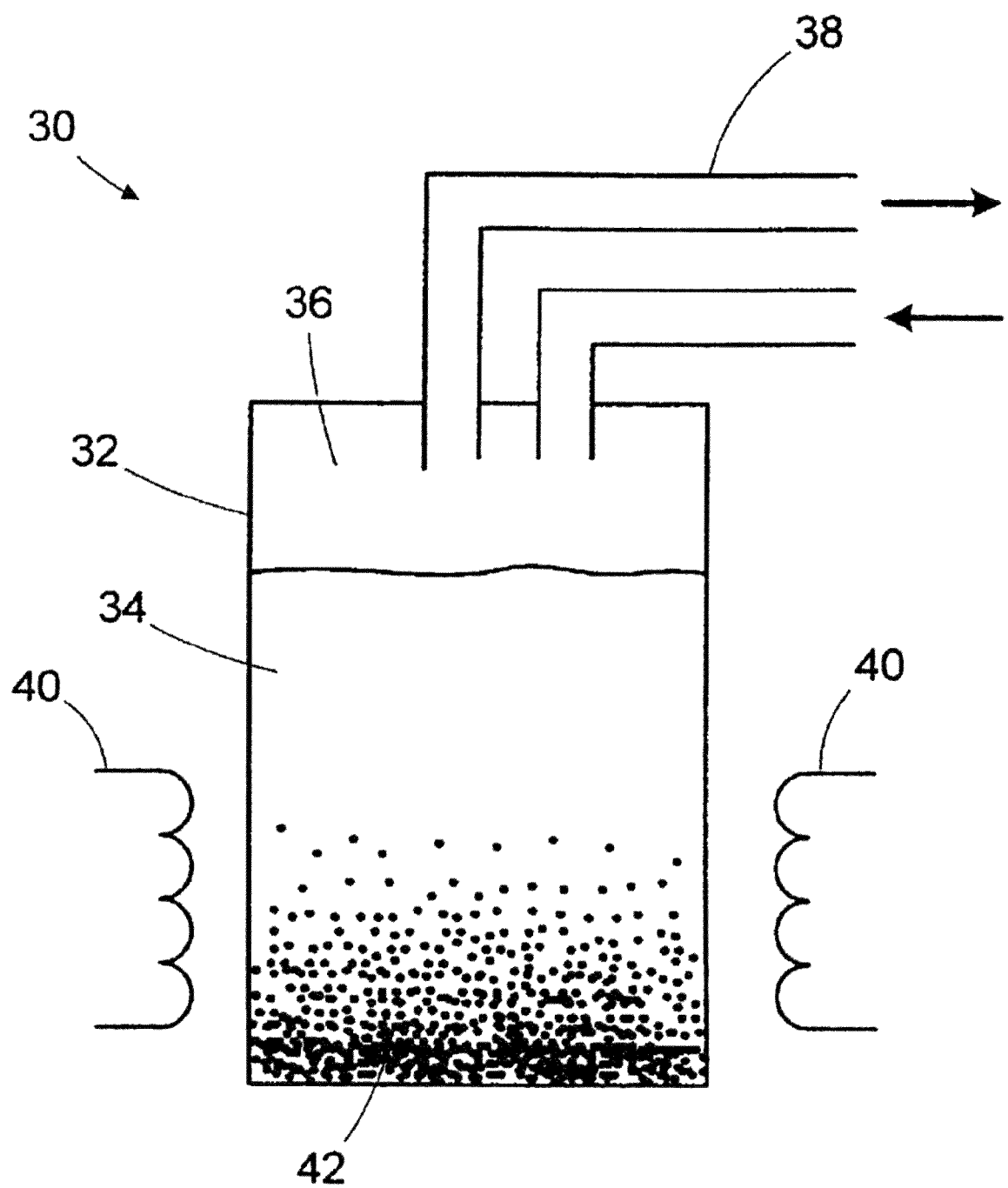
FIG. 2. Depiction of a preferred batch-type reactor useful for the described method.

FIG. 2 is a simplified diagram of a batch-type bioprocessing reactor 30 suitable for carrying out the inventive process shown in FIG. 1. The reactor includes a container 32 constructed of glass or other inert material. A culture medium 34 is introduced in the container 32. The culture medium 34 contains an aqueous solution of nutrients, trace elements, vitamins, and other organic and inorganic compounds as described in the foregoing examples. The solutions described above are provided for illustrative purposes. Other solution constructs are possible, depending on the specific implementation.

The container 32 is sealed to prevent the entry of air into the headspace gas region 36, thereby maintaining anaerobic conditions within the culture as well as permitting the inventive process to be carried out at pressures greater or less than ambient if desired. A gas conduit 38 is preferably included to allow the introduction of selected gases into the container and to allow gases to exit the container. A heating element 40 is preferably provided proximate to the container 32 to maintain the culture medium 34 at a desired temperature for growth of the anaerobic thermophilic bacteria. An electron donor is introduced into the culture (e.g., as a gas, such as hydrogen or CO) through the gas conduit 38, or dissolved directly into the culture medium 34 in the case of simple organics, such as glucose, lactate, and pyruvate. An electron acceptor (i.e., non-metal component) is provided in the form of one or more reducible species of S, Se, Te, or As, preferably dissolved or suspended in the culture medium 34. A source of a desired transition metal, preferably a chalcophile element such as Zn, Cd, Hg, Ga, In, Ag, W, Fe, Co, Cu, Ni, etc., is provided as either a soluble species or a suspended particulate. One or more additional dopant species, which may or may not be reducible, may be provided in the culture medium 34. The dopant species may be a metal, such as a small amount of Ag added in substitution for some of the Zn in ZnS (i.e., a ZnS:Ag doped composition), or Hg added in substitution for Cd in CdTe. Alternatively, substitutions may be made in the non-metal, such as replacing some of the S with Se and/or Te. Thus, the skilled artisan may vary the characteristics of the product over a wide range by selection of a variety of different dopants in a variety of different concentrations or molar ratios.

A crystalline product 42 forms in the container 32 as the bacteria reduces the reducible species. When a sufficient quantity of crystalline product 42 has been produced and allowed to settle to the bottom of the container 32, the culture medium 34 is preferably decanted and the crystalline product 42 collected and washed. The incubation may be between 3 and 30 days, depending on the amount and size of the crystalline product desired.

EXAMPLE 8

A Continuous-Type Bioprocessing Reactor

Figure 3:
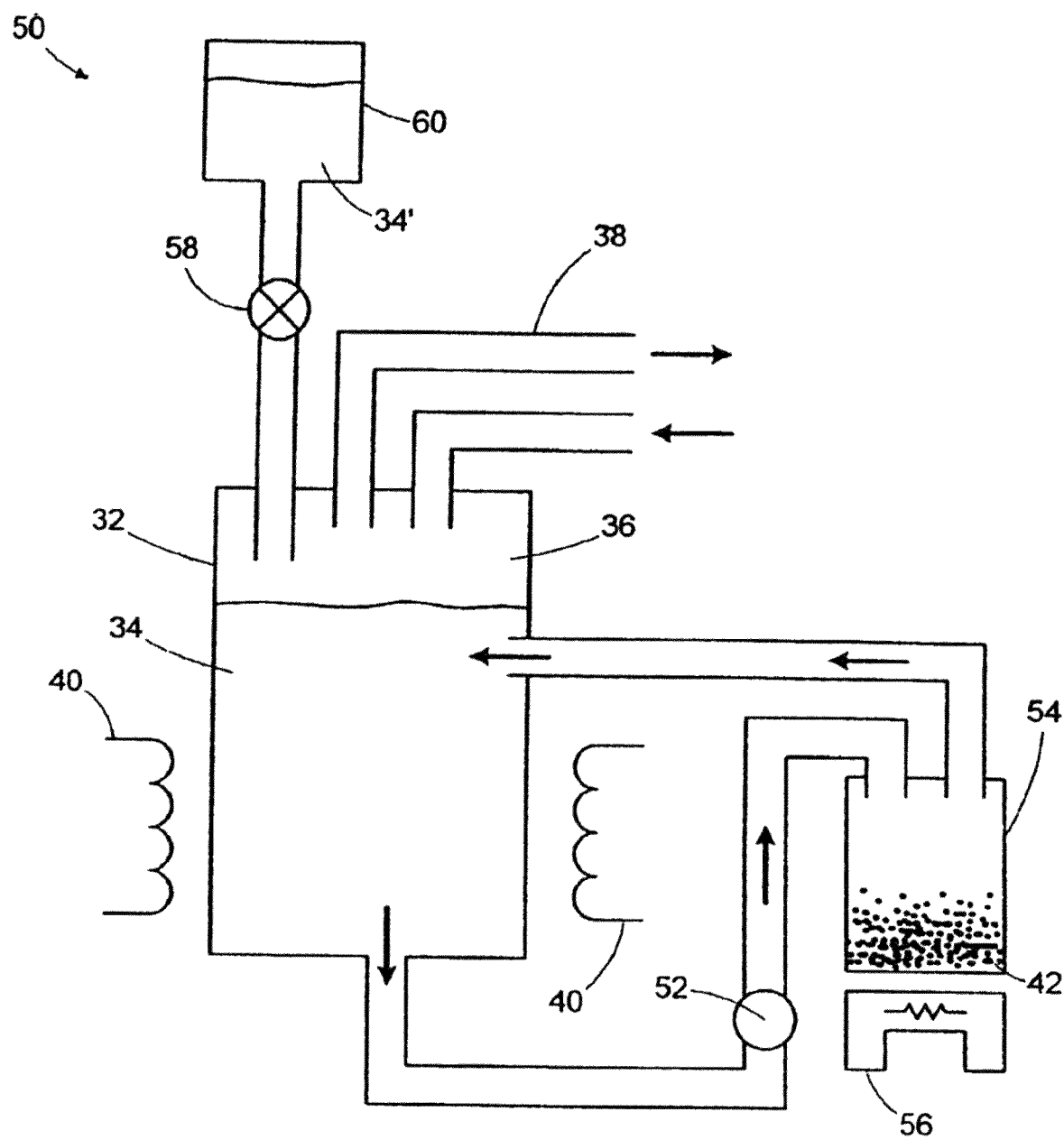
FIG. 3. Depiction of a continuous-type reactor useful for the described method.

The disclosed process may also be performed in a continuous arrangement as shown schematically by the bioreactor 50 shown in FIG. 3. The bioreactor 50 operates in a similar manner as the bioreactor 30 of FIG. 2. The bioreactor 50 preferably includes a fluid recirculator 52 that allows the culture medium 34 to pass through an external trap 54 from which the crystalline product 42 can be removed. The trap 54 may separate the crystalline product 42 from the circulating culture medium by settling, due to the greater density of the crystalline product 42. Continuous collection of product from the circulating fluid may also be used as a means of controlling particle size, because the particles tend to grow larger the longer they remain in the culture.

An additional fluid valve 58 may be provided through which additional culture medium or nutrients 34 may be added from an external reservoir 60 while maintaining the anaerobic conditions within the container 32. Furthermore, because the photoluminescence of quantum dots is generally a function of their size and composition, a source of UV light and a spectrophotometer may be provided to periodically or continuously analyze the circulating fluid so that product may be extracted when the photoluminescent values reach the desired values.

The composition of the culture medium 34 may be changed periodically in order to make crystalline products 42 of various selected compositions. The electron acceptor may be adjusted during the process, to make, for example, particles with a compositionally zoned or layered structure for special applications.

EXAMPLE 9

Figure 4:
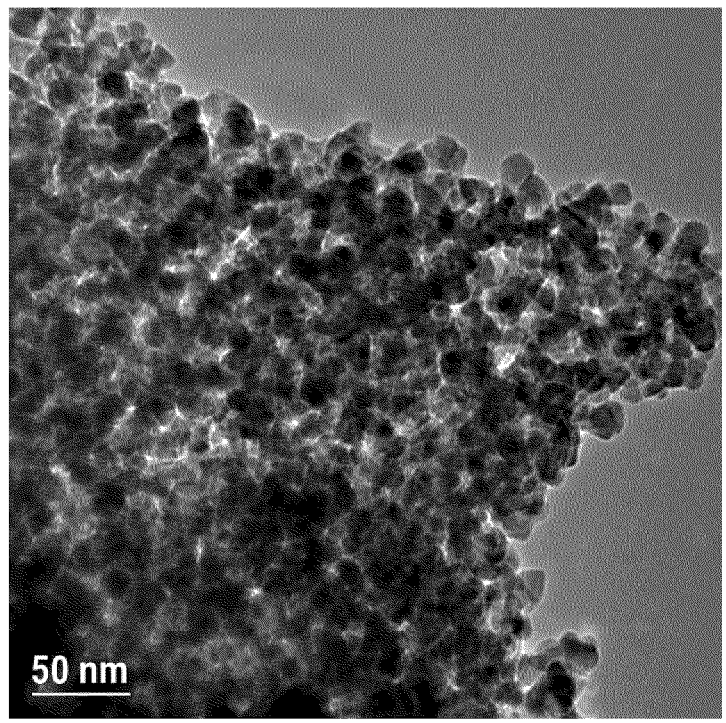
FIG. 4. TEM photographs of CdS nanoparticles produced by the invention using two different sources of sulfur and *Thermoanaerobacter* strain TOR-39.
Figure 4:
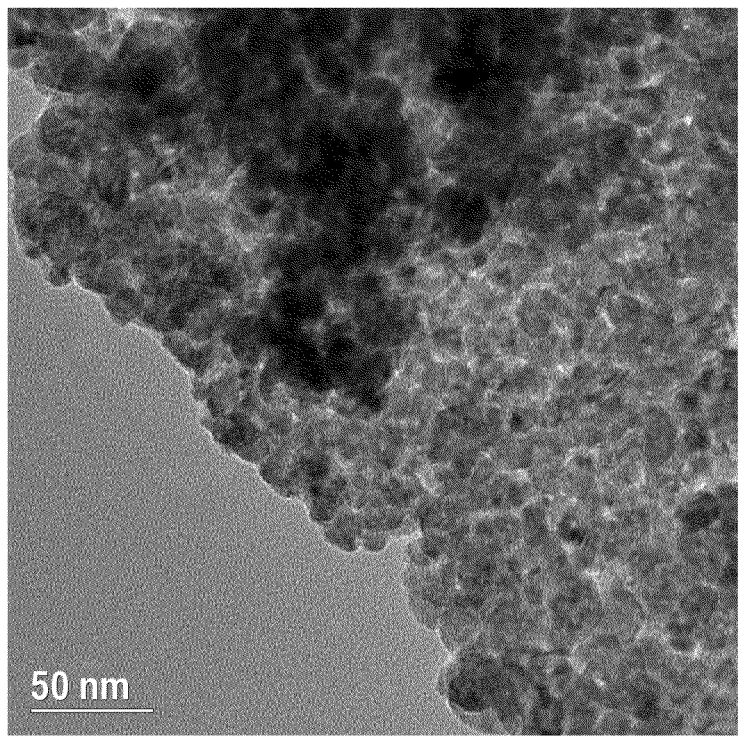

TEM and XRD Analysis of CdS Quantum Dots Produced According to the Invention FIG. 4 shows TEM photographs of exemplary CdS quantum dots formed in accordance with the present invention at a temperature of about 60° C. The particles clearly exhibit substantially equiaxed, euhedral crystallite morphology. The upper photo shows particles produced by TOR-39 using thiosulfate as the source of sulfur. XRD measurements determined that the predominant crystalline phase is hexagonal CdS (greenockite). The lower photo shows particles produced by TOR-39 using cysteine-S as the source of sulfur. XRD measurements indicate that the predominant crystalline phase is cubic CdS (hawleyite). This surprising result indicates not only that nanometer-sized particles can be synthesized by fermentative bacteria, but also that the choice of sulfur source can influence the particular crystalline phase when a compound can exist in more than one polymorph.

EXAMPLE 10

Figure 5:
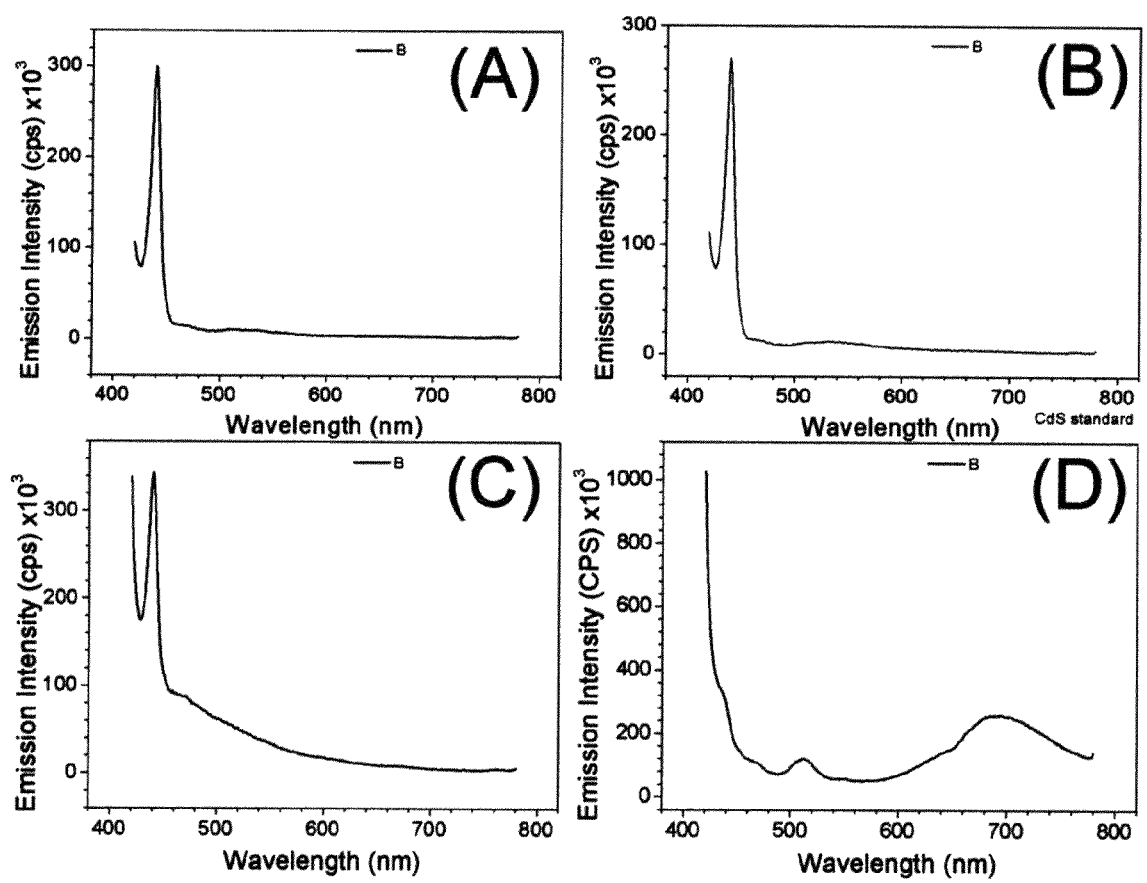
FIG. 5. Photoluminescence spectra of CdS produced using different precursor compounds and microbes: TOR-39 with thiosulfate (FIG. A) TOR-39 with sulfite (FIG. B), and *Desulfovibrio* sp. G-20 with $SO_3$ (FIG. C), as compared to standard CdS powder (FIG. D).

Fluorescence Analysis of CdS Quantum Dots Produced According to the Invention Optical fluorescence data collected on several batches of particles made using the invention are presented in FIG. 5 where it can be seen that the microbially-produced materials exhibit very sharp photoluminescence, with peaks having a FWHM around 10 nm. By comparison, FIG. 5D shows the photoluminescence spectrum for standard CdS powder having a particle size in the micron range. As shown, the standard CdS powder exhibits an extremely broad and poorly defined photoluminescence spectrum as compared to the CdS nanoparticles produced according to the present invention.

Figure 6:
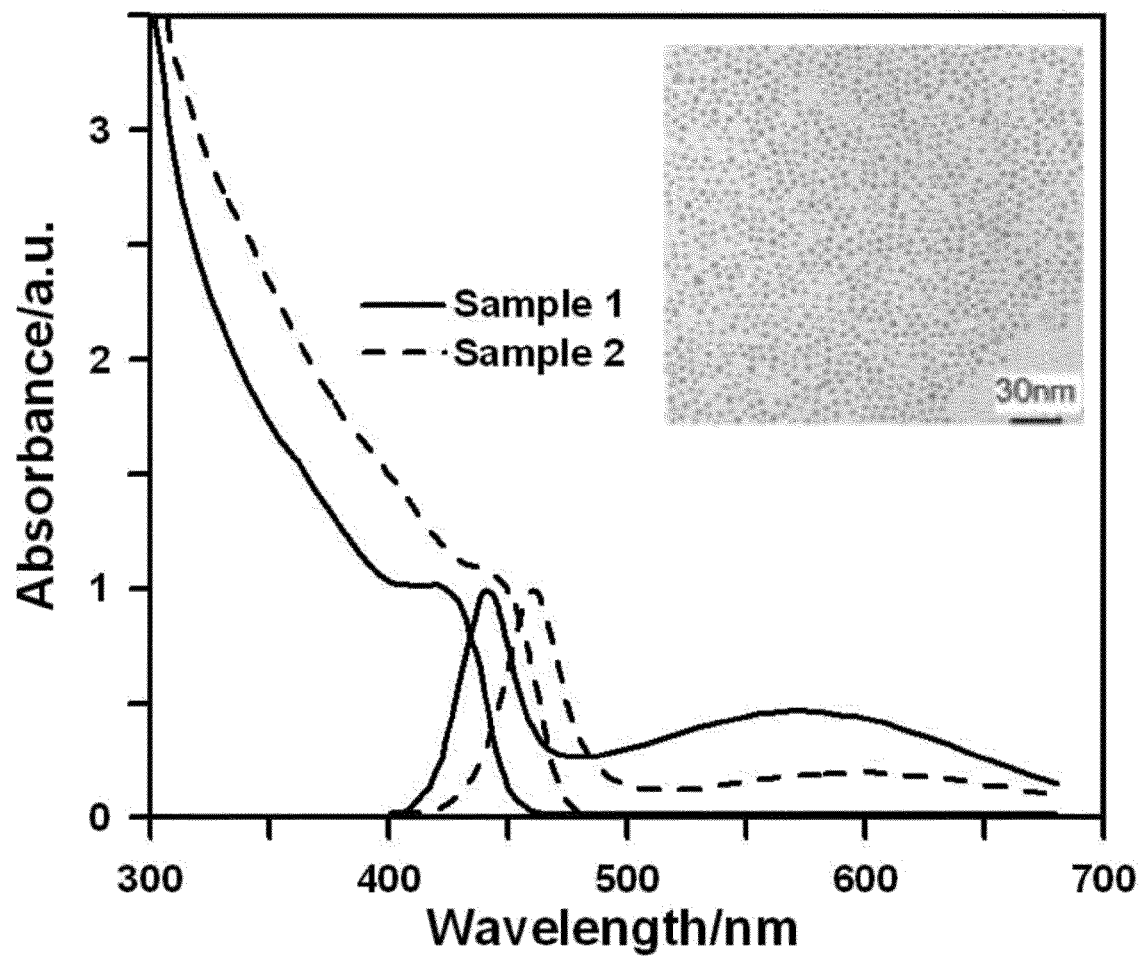
FIG. 6. Comparative photoluminescence spectra of CdS nanoparticles prepared by inorganic synthetic techniques of the prior art.

For further comparison, CdS quantum dots prepared inorganically by current state of the art methods (see, for example, Darugar et al., "Observation of optical gain in solutions of CdS quantum dots at room temperature in the blue region", *Appl. Phys. Lett,* 88: 261108 (2006)) exhibited photoluminescence peaks (as shown in FIG. 6) that were not nearly as sharp as those of the present invention (e.g., FWHM=28 nm). Accordingly, a roughly three-fold improvement has been provided by using the bacterially-mediated process of the invention.

It will be appreciated that process variables such as choice of electron donor and incubation time may be controlled to adjust the average crystallite size. Adjusting the crystallite size (and particularly the size distribution in a particular batch) will generally influence the observed photoluminescent behavior, and particularly, the sharpness of the PL peak. In particular, without being bound by any theory, it is believed that the sharpness of the PL peak of the nanoparticle compositions of the present invention can be attributed to either the increased size uniformity (i.e., monodispersity) or the increased uniformity in composition or crystalline morphology of the nanoparticles as compared to nanoparticle compositions of the art.

While there have been shown and described what are at present considered the preferred embodiments of the invention, those skilled in the art may make various changes and modifications which remain within the scope of the invention defined by the appended claims.

What is claimed is:

1. A method for producing non-oxide semiconductor nanoparticles, the method comprising:
   (a) subjecting a combination of reaction components to conditions conducive to microbially-mediated formation of non-oxide semiconductor nanoparticles, wherein said combination of reaction components comprises i) anaerobic thermophilic metal-reducing microbes selected from *Thermoanaerobacter, Thermoanaerobium, Thermoterrabacterium, Thermococci,* and *Deinococcus-Thermus,* ii) a culture medium suitable for sustaining said anaerobic microbes, iii) a chalcophile metal component comprising at least one type of metal ion that is microbially non-reducible selected from Cd, Cu, Ga, In, and Zn, iv) a non-metal component containing at least one non-metal selected from the group consisting of S, Se, and Te, wherein said non-metal component does not include sulfate, and v) one or more electron donors that provide donatable electrons to said anaerobic microbes during consumption of the electron donor by said anaerobic microbes; and
   (b) isolating said non-oxide semiconductor nanoparticles, which have a composition selected from CdS, CdSe, CdTe, ZnS, ZnSe, ZnTe, $Ga_2S_3$, $Ga_2Se_3$, $Ga_2Te_3$, $In_2S_3$, $In_2Se_3$, $In_2Te_3$, $Ga_xIn_{2-x}Se_3$, CuS, CuSe, CuTe, $Cd_xZn_{1-x}Se$, $Cd_xZn_{1-x}Te$, $CuIn_xGa_{1-x}S_2$, $CuIn_xGa_{1-x}Se_2$, $CuGaS_2$, $CuInS_2$, $CuGaSe_2$, and $CuInSe_2$, wherein x is an integral or non-integrel numerical value greater than 0 and less than or equal to 1.

2. The method of claim 1, wherein said non-metal component includes a reducible sulfur-containing, selenium-containing, or tellurium-containing compound.

3. The method of claim 2, wherein said reducible sulfur-containing compound is a sulfite or thiosulfate compound.

4. The method of claim 2, wherein said reducible selenium-containing compound is a selenate, selenite, or selenosulfate compound.

5. The method of claim 2, wherein said reducible tellurium-containing compound is a tellurate or tellurite compound.

6. The method of claim 2, wherein said non-metal component comprises a sulfur-containing, selenium-containing, or tellurium-containing amino acid or nucleic base.

7. The method of claim 1 wherein said one or more electron donors include one or more carboxylate-containing compounds that can be oxidatively consumed by the microbes.

8. The method of claim 1 wherein said one or more electron donors include one or more sugar compounds that can be oxidatively consumed by the microbes.

9. The method of claim 1 wherein said one or more electron donors include one or more oxidizable gaseous compounds or elements that can be oxidatively consumed by the microbes.

10. The method of claim 1 wherein the non-oxide semiconductor nanoparticles possess a size within a range of about 1 nm to about 500 nm.

11. The method of claim 1 wherein the non-oxide semiconductor nanoparticles possess a size within a range of about 1 nm to about 200 nm.

12. The method of claim 1 wherein the non-oxide semiconductor nanoparticles possess a size within a range of about 1 nm to about 100 nm.

13. The method of claim 1 wherein the non-oxide semiconductor nanoparticles possess a size within a range of about 1 nm to about 20 nm.

14. The method of claim 1 wherein the non-oxide semiconductor nanoparticles possess a size within a range of about 1 nm to about 10 nm.

15. The method of claim 1, wherein the method is conducted at a temperature of at least 40° C.

16. The method of claim 1, wherein said anaerobic microbes are mesophilic or psychrotolerant, and said method is conducted at a temperature of less than 40° C.

17. The method of claim 1, wherein said non-metal component is comprised of one or more inorganic compounds selected from inorganic sulfur-containing, selenium-containing, and tellurium-containing, compounds.

18. The method of claim 1, wherein said non-metal component is comprised of one or more organic compounds selected from organosulfur, organoselenium, and organotellurium, compounds.

19. The method of claim 1, wherein said thermophilic metal-reducing microbes are in the genus *Thermoanaerobacter*.

\* \* \* \* \*